United States Patent
Ohga et al.

(10) Patent No.: US 10,271,804 B2
(45) Date of Patent: Apr. 30, 2019

(54) X-RAY IMAGE DIAGNOSIS APPARATUS

(71) Applicant: Toshiba Medical Systems Corporation, Otawara-shi (JP)

(72) Inventors: Nobuhiro Ohga, Nasushiobara (JP); Jun Okada, Nasushiobara (JP); Satoru Esashi, Nasushiobara (JP); Toshio Muroi, Nasushiobara (JP); Nobuo Ogura, Otawara (JP); Masanori Gunji, Otawara (JP); Yasuto Hayatsu, Otawara (JP); Ryoichi Nagae, Nasushiobara (JP); Yoshiaki Iijima, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 170 days.

(21) Appl. No.: 15/225,092

(22) Filed: Aug. 1, 2016

(65) Prior Publication Data
US 2017/0112456 A1  Apr. 27, 2017

(30) Foreign Application Priority Data
Oct. 27, 2015  (JP) ................................. 2015-211166

(51) Int. Cl.
*A61B 6/00* (2006.01)
*A61B 6/06* (2006.01)

(52) U.S. Cl.
CPC .............. *A61B 6/4266* (2013.01); *A61B 6/06* (2013.01); *A61B 6/4441* (2013.01);
(Continued)

(58) Field of Classification Search
CPC .............................. A61B 6/482; G01T 1/2985
See application file for complete search history.

(56) References Cited

U.S. PATENT DOCUMENTS

| | | | | |
|---|---|---|---|---|
| 2003/0169847 A1* | 9/2003 | Karellas | ................. | A61B 6/481 378/98.3 |
| 2007/0114426 A1* | 5/2007 | Tkaczyk | ............... | G01T 1/2018 250/370.09 |

(Continued)

FOREIGN PATENT DOCUMENTS

| JP | 2012-223629 | 11/2012 |
|---|---|---|
| JP | 2014-144053 | 8/2014 |

(Continued)

*Primary Examiner* — Kenneth J Malkowski
(74) *Attorney, Agent, or Firm* — Oblon, McClelland, Maier & Neustadt, L.L.P.

(57) ABSTRACT

According to one embodiment, the X-ray image diagnosis apparatus comprises an X-ray generator, an X-ray restriction unit, a first X-ray detector, a second X-ray detector, and a drive. The X-ray generator generates X-rays to be applied to a subject. The X-ray restriction unit is disposed between the subject and the X-ray generator to restrict X-rays outside an opening region which is formed using a metal plate. The first X-ray detector has a first detection region in which X-rays that pass through the subject are detected. The second X-ray detector has a second detection region which is smaller than the first detection region and which has a high spatial resolution. The drive moves the first and second X-ray detectors so that the second detection region includes an irradiation region of the subject formed by the opening region.

17 Claims, 11 Drawing Sheets

(52) U.S. Cl.
CPC ............ *A61B 6/4452* (2013.01); *A61B 6/461* (2013.01); *A61B 6/463* (2013.01); *A61B 6/469* (2013.01); *A61B 6/487* (2013.01); *A61B 6/54* (2013.01); *A61B 6/587* (2013.01); *A61B 6/504* (2013.01)

(56) References Cited

U.S. PATENT DOCUMENTS

| | | | | |
|---|---|---|---|---|
| 2011/0080993 | A1* | 4/2011 | Hoffman | A61B 6/032 378/19 |
| 2014/0037045 | A1* | 2/2014 | Dafni | A61B 6/032 378/5 |
| 2014/0051991 | A1 | 2/2014 | Sakaguchi et al. | |
| 2015/0139382 | A1 | 5/2015 | Hyung et al. | |

FOREIGN PATENT DOCUMENTS

| | | |
|---|---|---|
| JP | 2014-237041 | 12/2014 |
| JP | 2015-97782 | 5/2015 |
| JP | 5731888 | 6/2015 |

* cited by examiner

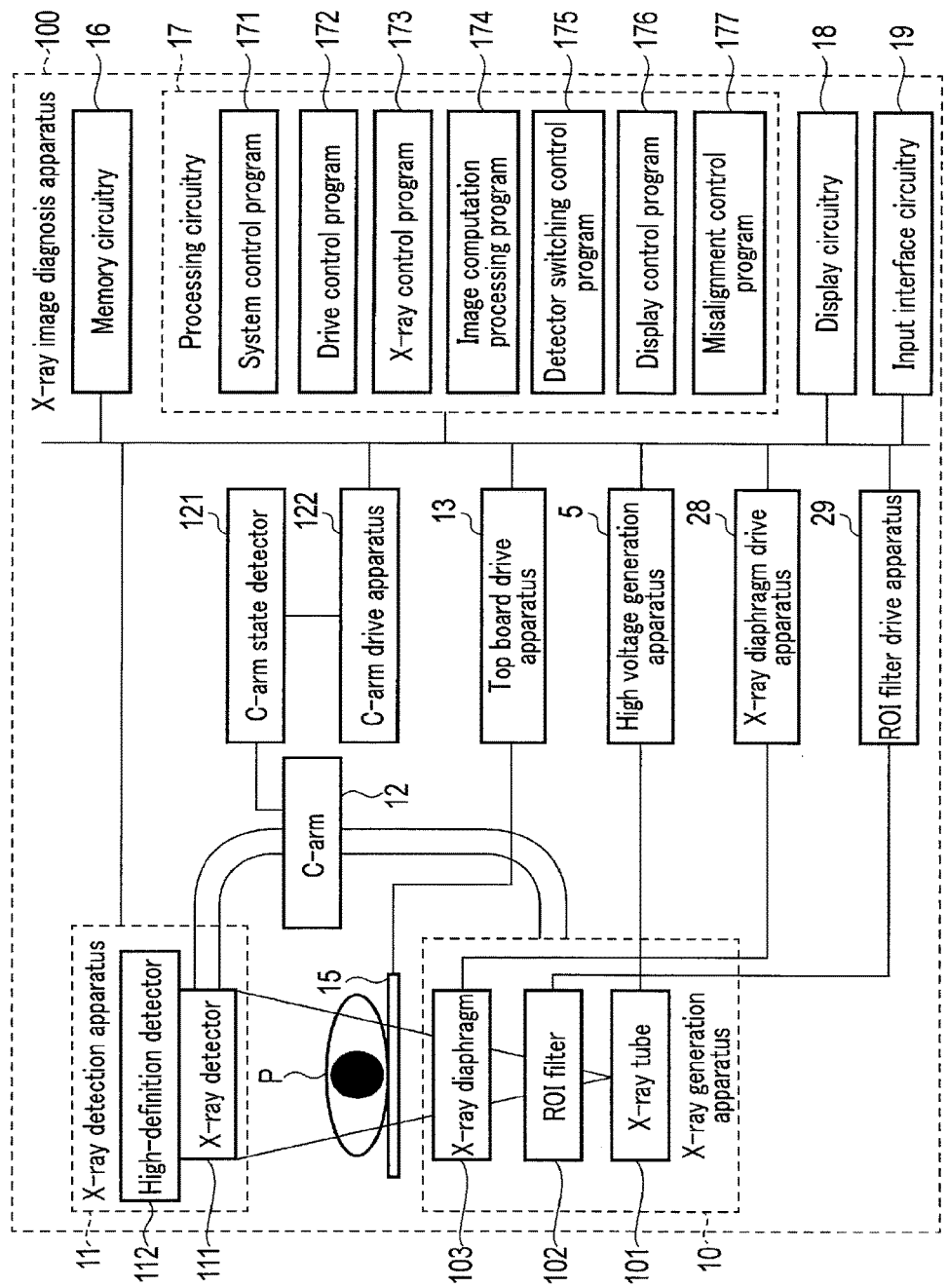
F I G. 1

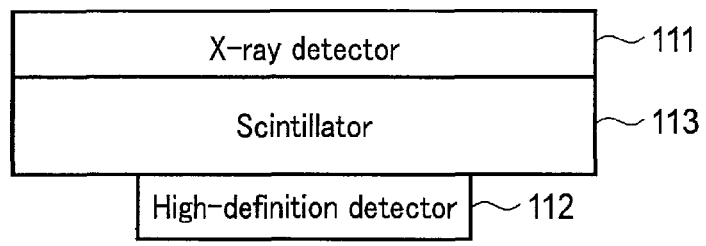
F I G. 2A
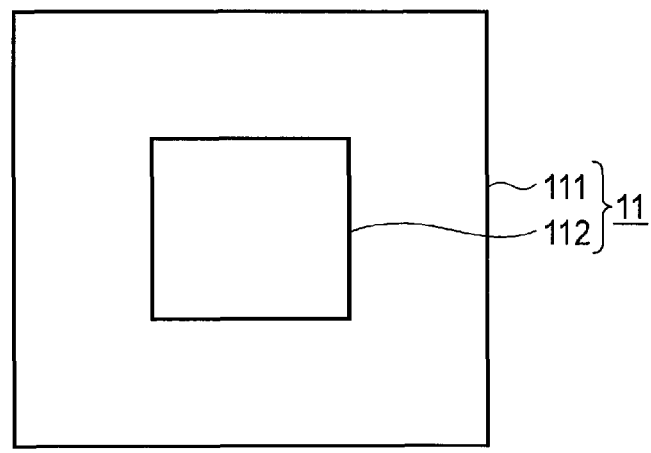
F I G. 2B

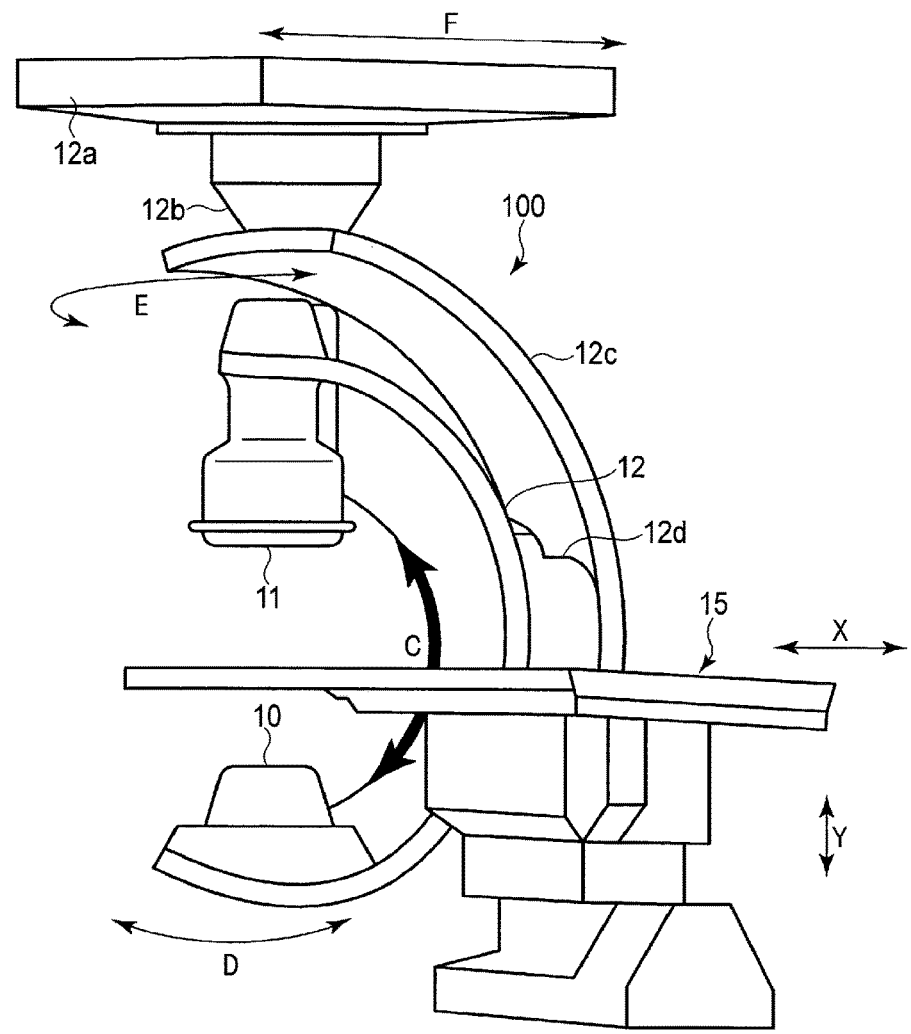
F I G. 3A

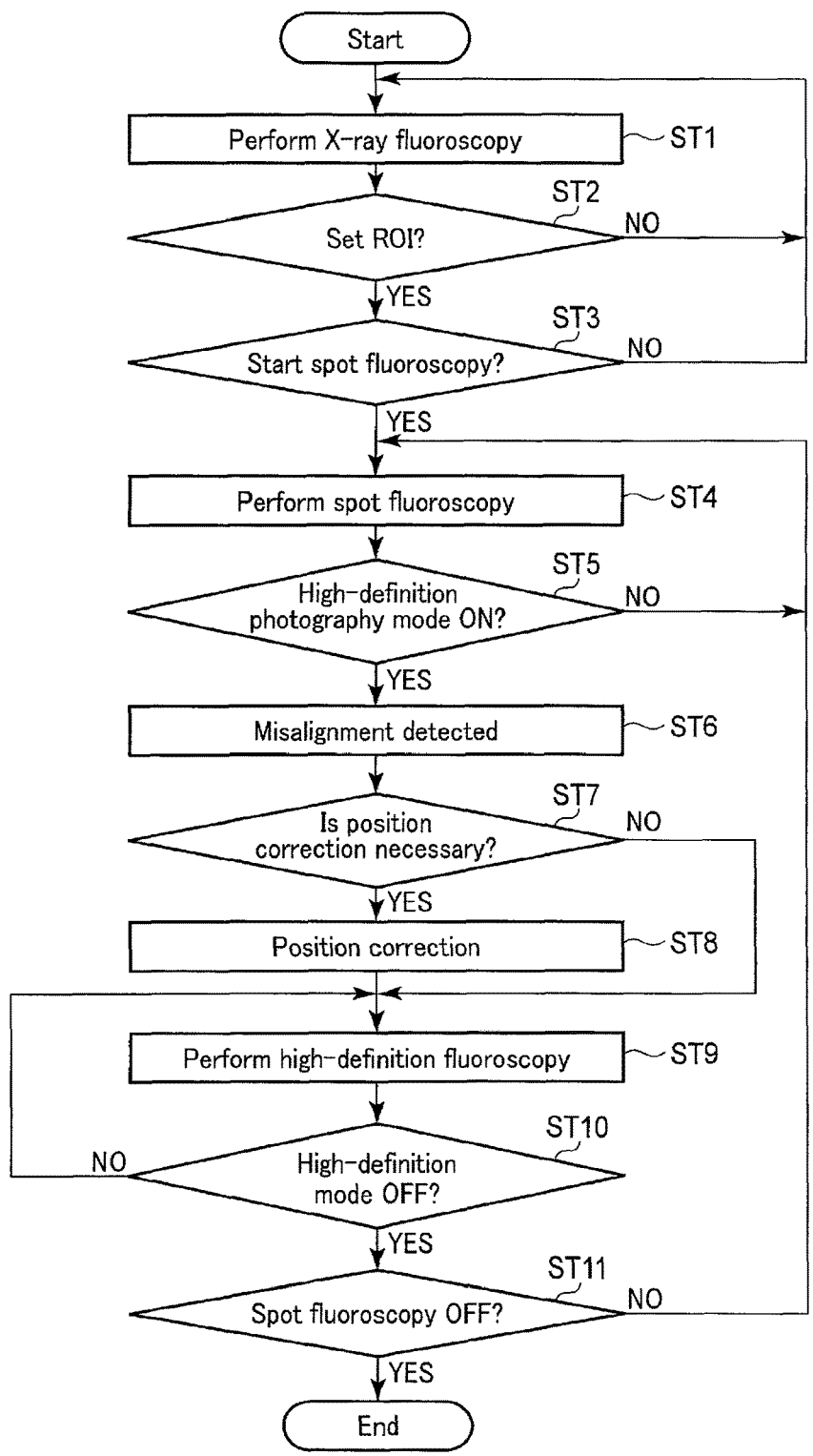
F I G. 4

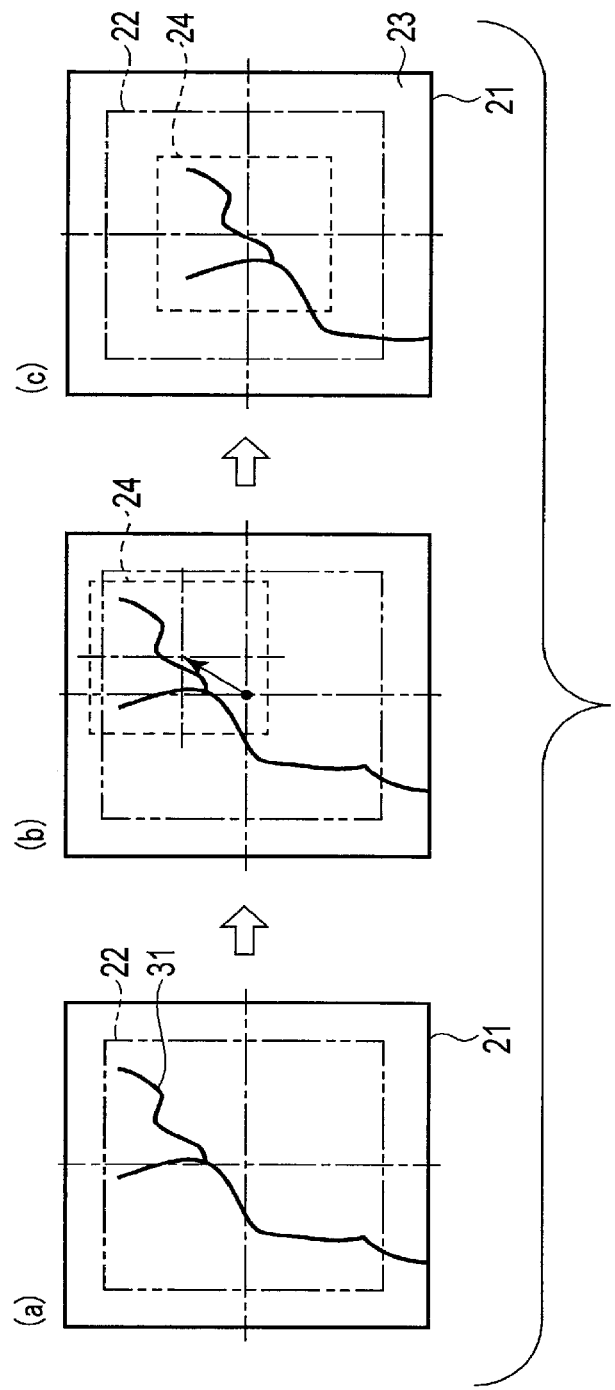
F I G. 5

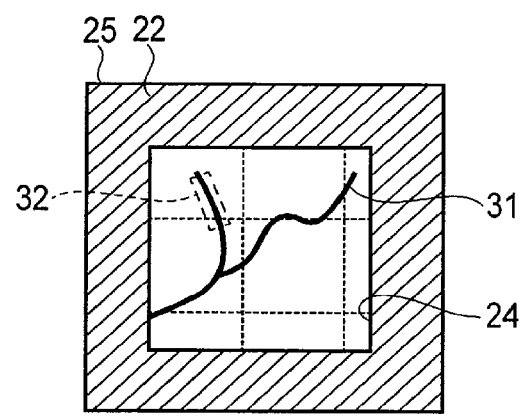
F I G. 6

X-RAY IMAGE DIAGNOSIS APPARATUS

CROSS-REFERENCE TO RELATED APPLICATIONS

This application is based upon and claims the benefit of priority from prior Japanese Patent Application No. 2015-211166, filed on Oct. 27, 2015, the entire contents of which are incorporated herein by reference.

FIELD

Embodiments described herein relate generally to an X-ray image diagnosis apparatus.

BACKGROUND

In a conventional X-ray image diagnosis apparatus, a C-arm supports a pair of an X-ray generation apparatus and an X-ray detection apparatus being opposed each other. In recent years, an approach has been taken to improve diagnosis and treatment techniques through adopting an MAF (Micro Angiographic Fluoroscope) in this conventional X-ray detection apparatus to obtain a high-definition image of a small ROI (Region of Interest), such as a lesion. As this type of X-ray detection apparatus, a configuration equipped with, in addition to an X-ray detector having an eight to twelve-inch screen with a normal pixel size, a high-definition X-ray detector having many detection elements and a small-sized screen in the size of four to six inches with a smaller pixel size compared to a usual X-ray detector, is known. Specifically, there is a one-panel configuration in which a normal X-ray detector and a high-definition X-ray detector are integrated, and a two-panel configuration in which a normal X-ray detector and a high-definition X-ray detector are separately driven.

Spot fluoroscopy and ROI fluoroscopy techniques are known as an X-ray fluoroscopy technique using a catheter. In spot fluoroscopy, an X-ray diaphragm is controlled so that X-rays are irradiated only on an ROI designated by an operator, and X-rays outside of the ROI are shielded. Since X-rays irradiated outside of the ROI are shielded in the spot fluoroscopy, the exposure dose of a subject can be reduced. ROI fluoroscopy is a technique of X-ray irradiation which is carried out with an ROI filter being disposed, which has an opening region at least in a part, and is made of copper or aluminum, etc. Accordingly, the exposure of the X-rays passed through the ROI filter are attenuated in comparison to those in the opening region which is the ROI, thereby reducing an exposure dose of the subject.

When the aforementioned fluoroscopy technique and image display using the high-definition detector are performed in combination, it is necessary to match the ROI on which an operator carries out fluoroscopy with a detection region of the high-definition detector. This requires a position of the high-definition detector to be designated on an image in a manner so that a pre-set detection region of the high-definition detector matches with the ROI.

BRIEF DESCRIPTION OF THE DRAWINGS

FIG. 1 is a block diagram showing the configuration of the X-ray image diagnosis apparatus according to the embodiment.

FIG. 2A is a diagram showing an example of the X-ray detector comprising the high-definition detector according to the embodiment.

FIG. 2B is a diagram showing another example of the X-ray detector comprising a high-definition detector.

FIG. 3A is a schematic view of a mechanism for moving the C-arm according to the embodiment.

FIG. 4 is a flowchart of automatic positioning to a spot/ROI fluoroscopic region according to the embodiment.

FIG. 5 is a diagram showing an example of the automatic positioning mechanism at the time of carrying out spot fluoroscopy at the X-ray image diagnosis apparatus according to the embodiment.

FIG. 6 is a diagram showing an example of a display region after the spot radioscopy is carried out according to the embodiment.

DETAILED DESCRIPTION

Figure 3B:
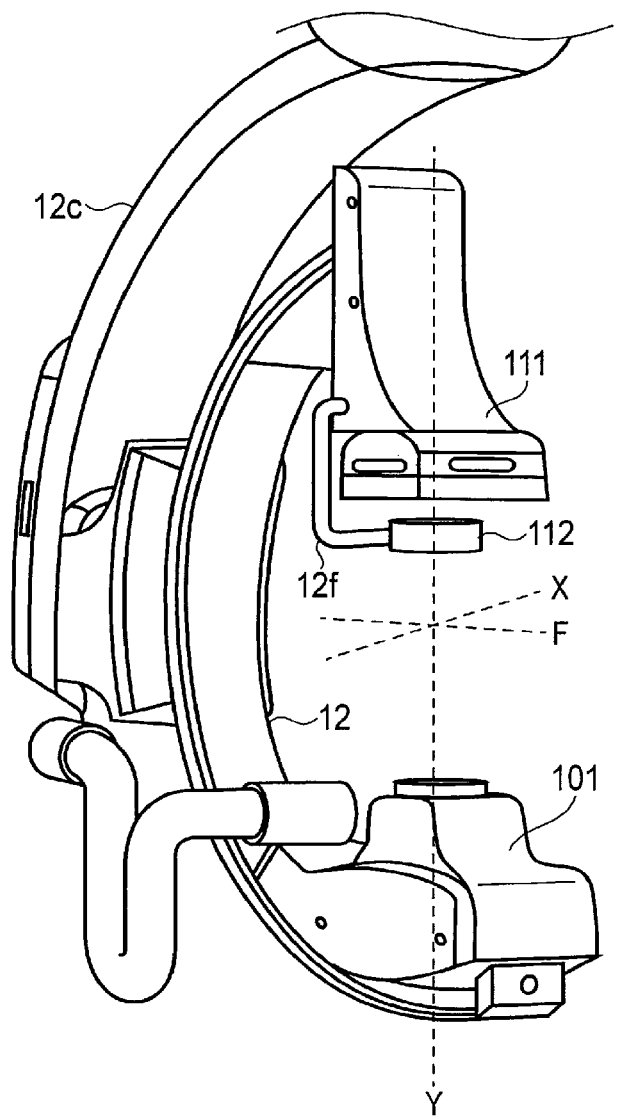
FIG. 3B is a schematic view of a mechanism for moving the high-definition detector according to the embodiment.

According to one embodiment, the X-ray image diagnosis apparatus comprises an X-ray generator, an X-ray restriction unit, a first X-ray detector, a second X-ray detector, and a drive. The X-ray generator generates X-rays to be applied to a subject. The X-ray restriction unit is disposed between the subject and the X-ray generator to restrict X-rays outside an opening region which is formed using a metal plate. The first X-ray detector has a first detection region in which X-rays that pass through the subject are detected. The second X-ray detector has a second detection region which is smaller than the first detection region and which has a high spatial resolution. The drive moves the first X-ray detector and the second X-ray detector so that the second detection region includes an irradiation region of the subject formed by the opening region based on a position of the opening region.

Hereinafter, an embodiment will be described with reference to the drawings.

FIG. 1 is a block diagram illustrating the configuration of the X-ray image diagnosis apparatus according to the embodiment. The X-ray image diagnosis apparatus 100 shown in FIG. 1 comprises a high voltage generation apparatus 5, an X-ray generation apparatus 10 which applies X-rays to a subject P, and an X-ray detection apparatus 11 which detects X-rays which pass through the subject P and generates X-ray projection data to which a detected X-ray dose is reflected, an X-ray diaphragm drive apparatus 28 which controls driving of an X-ray diaphragm 103, and an ROI filter drive apparatus 29 which carries out drive control of the ROI filter 102.

The high voltage generation apparatus 5 generates a high voltage to be applied between an anode and a cathode and outputs the high voltage to an X-ray tube 101 in order to accelerate thermal electrons generated at the cathode of the X-ray tube 101.

The X-ray generation apparatus 10 comprises the X-ray tube 101, the ROI filter 102 having a function of attenuating or reducing an exposure, and the X-ray diaphragm 103. The X-ray tube 101 is a vacuum tube for generating X-rays, and the tube accelerates thermal electrons emitted from the cathode (filament) due to a high voltage, and generates X-rays by colliding the accelerated electrons against a tungsten anode.

The ROI filter 102 is located between the X-ray tube 101 and the X-ray diaphragm 103, and made of a metal plate, such as copper and aluminum, etc. The ROI filter 102 has an opening region at least partially in the center, for example, and attenuates X-rays passing outside the opening region. Thus, the ROI filter 102 transmits all the X-rays in the X-ray transmitting region in the opening region, and attenuates X-rays transmitted in the other regions.

The X-ray diaphragm 103 is located between the X-ray tube 101 and the X-ray detection apparatus 11, and is made of a lead plate. The X-ray diaphragm 103 shields X-rays transmitted outside the opening region and narrows the passage of X-rays generated by the X-ray tube 101 so that the X-rays are applied only to the ROI of the subject P. The X-ray diaphragm 103 has four blades, for example, and slides the blades to adjust the region to shield X-rays to a desired size. Herein, each of the ROI filter 102 and the X-ray diaphragm 103, which is provided between the subject and the X-ray tube 101 and has an opening region formed on a metal plate, realizes the X-ray restriction unit which restricts X-rays outside the opening region.

The X-ray detection apparatus 11 comprises a flat-plane X-ray detector 111 which converts X-rays that have passed through the subject P into a charge and accumulates the charge, and a high-definition detector 112 which is a type of X-ray detection device capable of detecting X-rays with high definition (high resolution) compared to the X-ray detector 111. The X-ray detector 111 includes a FPD, for example. The size of the FPD is generally eight to twelve inches. The FPD is composed of micro detection elements aligned two-dimensionally, in a column direction and a line direction. Each detection element is composed of a photoelectric film which senses X-rays and generates a charge in accordance with an amount of incident X-rays, a charge accumulating capacitor which accumulates the charge generated on the photoelectric film, and a thin-film transistor (TFT) which outputs the charge accumulated at the charge accumulating capacitor at a predetermined timing.

The high-definition detector 112 is an X-ray detector which has a higher spatial resolution than the X-ray detector 111. For example, the high-definition detector 112 has more detection elements per a unit area than the X-ray detector 111 does, and it usually is a detector having four or more times as many detector elements as a regular detector. The high-definition detector 112 has a detection region of four to six inches, which is smaller than that of the X-ray detector 111. The high-definition detector 112 has a configuration in which a scintillator is formed on a CCD (charge coupled device) formed on a monocrystal Si substrate, for example. A CCD is one aspect of an image sensor, and it generates charge in accordance with an amount of incident X-rays when X-rays are incident on a monocrystal Si substrate. A CMOS (complementary metal-oxide-semiconductor) image sensor may be used instead of a CCD for the high-definition detector 112. A CMOS is also one aspect of an image sensor, and it generates a charge upon incidence of X-rays on a monocrystal Si substrate, similarly to a CCD, in accordance with the amount of incident X-rays. In addition, a CMOS accumulates the generated charge as a capacity, and converts the charge into voltage components to output.

As a configuration of the X-ray detection apparatus 11, a one-panel configuration in which the X-ray detector 111 and a high-definition detector 112 are integrated as shown in FIG. 2A may be adopted. In the one-panel X-ray detection apparatus 11, the scintillator 113, which has a function of converting incident X-rays into light, is arranged interposed between and opposed to the X-ray detector 111 and the high-definition detector 112. In other words, the high-definition detector 112 may be attached in such a manner that the detection region of the high-definition detector 112 overlaps the detection region of the X-ray detector 111. With such a configuration, when X-rays are incident on a position where the X-ray detector 111 and the high-definition detector 112 are opposed to one another, both of the X-ray detector 111 and the high-definition detector 112 detect light, and when X-rays are incident only on the region of the X-ray detector 111, which is outside the opposing position, only the X-ray detector 111 detects X-rays.

The configuration of the X-ray detection apparatus 11 in the present embodiment is not limited to the aforementioned configuration. For example, two detectors may be disposed on the same plane, instead of the X-ray detector 111 and the high-definition detector 112 being oppositionally arranged to one another. In this case, as shown in FIG. 2B, the high-definition detector 112 is disposed inside the X-ray detector 111 to constitute one X-ray detection apparatus 11 on the same plane. In other words, the high-definition detector 112 may be disposed inside the X-ray detector 111, and may be attached integrally with the X-ray-detector 111. As another configuration, a two-panel configuration in which the X-ray detector 111 and the high-definition detector 112 are separately driven, and in which the high-definition detector 112 is disposed in front of the X-ray detector 111 in a retractable manner so that the high-definition detector 112 is used only when necessary, may be adopted. In other words, the high-definition detector 112 may be disposed separately from the X-ray detector 111, so that the high-definition detector 112 can move independently from the X-ray detector 111. It should be noted that, although not shown in the drawings, the X-ray detection apparatus 11 comprises a projection data generation unit. The X-ray detection apparatus 11 outputs the charge accumulated in the X-ray detector 111 and the high-definition detector 112. The projection data generation unit generates X-ray projection data in accordance with the output charge from the X-ray detector 111 and the high-definition detector 112.

The X-ray diaphragm drive apparatus 28 drives the aperture blades of the X-ray diaphragm 103 to control the opening region of the X-ray diaphragm 103. Specifically, driving of the aperture blades is controlled in such a manner that the ROI input by the operator through the input interface circuitry 19 matches with the X-ray irradiation region. The X-ray diaphragm drive apparatus 28 also has a function of detecting an opening formed by the X-ray diaphragm 103. A method of detecting an opening region formed by the X-ray diaphragm 103 can be detecting the size of the opening region, or detecting an amount of movement of the aperture blades.

The ROI filter drive apparatus 29 drives the ROI filter 102 to set an ROI fluoroscopic region 26 for the ROI which was input by the operator through the input interface circuitry 19. The ROI fluoroscopy is carried out by driving the ROI filter 102 between the X-ray tube 101 and the subject P.

The X-ray image diagnosis apparatus 100 has a C-arm 12, a C-arm state detector 121, a C-arm drive apparatus 122, and a top board drive apparatus 13.

The C-arm 12 holds the X-ray generation apparatus 10 and the X-ray detection apparatus 11 in such a manner that they are opposed to each other with the subject P and the top board 15 being interposed therebetween, thereby having a structure for performing X-ray photography on the subject P on the top board 15.

As shown in FIG. 3A, a pedestal 12a is disposed on the ceiling plane, and the pedestal 12a is moved thereon in a horizontal direction (the arrow F) along a rail (not shown). A supporting point 12b is coupled to the pedestal 12a, and a stationary arm 12c is rotated about the axis extending from the supporting point 12b toward the floor plane to rotate the stationary arm 12c in a horizontal direction with respect to the ceiling plane (the arrow E). A connecting portion 12d holds the C-arm 12 in such a manner that the C-arm 12 can slide along the shape of the C-arm 12 (the arrow C), and the C-arm 12 is rotated about the axis extending in parallel with the ceiling plane from the connecting portion 12d to rotate the C-arm 12 (the arrow D) with respect to the stationary arm 12c. The above structure allows the C-arm 12 to make a translational movement in the direction indicated by the arrow F. It should be noted that the C-arm 12 and the pedestal 12a can move closer or away from the ceiling plane, in addition to the above-described movements.

In the case where the X-ray detection apparatus 11 has the two-panel configuration, the C-arm 12 may have an arm 12f which has a high-definition detector 112 at its distal end as shown in FIG. 3B, and is rotatably pivoted at its proximal end in the proximity of the X-ray detection apparatus 111. In this case, the proximal end of the arm 12f is controlled by a drive mechanism (not shown) in such a manner that the high-definition detector 112 is disposed in front of the X-ray detector 111 when needed and is removed when unneeded, for example.

The C-arm 12 is provided with a plurality of power sources disposed at desired locations in order to realize the movements as indicated respectively by the arrows C, D, E, and F shown in FIG. 3A, and these power sources constitute the C-arm drive apparatus 122. The C-arm 12 is provided with a C-arm state detector 121 to detect information of an angle, a posture, and a position of the C-arm 12. The C-arm state detector 121 is configured with a potentiometer which detects a rotation angle and an amount of movement and an encoder which is a position detection sensor, and the like. Specifically, a so-called absolute encoder, such as a magnetic encoder, a brush encoder, or a photo encoder, may be used an encoder. The C-arm state detector 121 according to the present embodiment may be configured with various types of position detection mechanisms, such as a rotary encoder which outputs rotation displacement as a digital signal, or a linear encoder which outputs linear displacement as a digital signal. These mechanisms for realizing movement of the C-arm 12 may be applicable, in a similar manner, to the mechanism for realizing movement of the high-definition detector 112 which is shown in FIG. 3B. The movement of both of the X-ray detector 11 and the high-definition detector 112, or the movement of the high-definition detector 112, which is realized by those mechanisms, is carried out based on information input by the operator, for example.

The above-described mechanisms for moving the C-arm 12 and the high-definition detector 112 are merely an example, and the present embodiment is not limited thereto. For example, in the above example, the movement of the C-arm 12 in the direction indicated by the arrow F in FIG. 3A is realized by a running-on-ceiling method in which the pedestal 12a runs along a rail provided on the ceiling; however, the movement in the direction indicated by the arrow F may be realized by moving a support pillar which is disposed on the floor plane and provided to hold the C-arm 12 on the floor plane.

The C-arm drive apparatus 122 reads a drive signal from a processing function of a drive control program 172 to have the C-arm 12 carry out a slide motion, a rotational motion, and a linear motion. The C-arm drive apparatus 122 is configured with a power source, such as a plurality of motors, etc. The top board drive apparatus 13 reads a drive signal from a processing function of the drive control program 172 to move the top board 15 in a horizontal or vertical direction with respect to the floor plane. The position relationship between the X-ray generation apparatus 10 and the X-ray detection apparatus 11 with respect to the subject P is changed as a result of the movement of the C-arm 12 or the top board 15.

The X-ray image diagnosis apparatus 100 has memory circuitry 16, processing circuitry 17, display circuitry 18, and input interface circuitry 19.

The memory circuitry 16 stores projection data generated using X-ray detection data detected by the X-ray detection apparatus 11 and X-ray image data generated from the projection data, and stores processing functions performed by the processing circuitry 17 in the form of a program.

The display circuitry 18 comprises a fluoroscopy monitor for displaying a variety of X-ray image data, a reference monitor for displaying an image of a different modality, etc., and a system monitor for displaying a variety of input and setting screens to input photography conditions, etc. and to control the system. These monitors may be configured separately, or may be realized by dividing a display area of a large monitor.

The input interface circuitry 19 may be comprised of an input device such as a trackball, a joystick, a main console having various buttons, a keyboard, and a mouse, etc., and a foot switch, and the like. With these input interfaces, input of subject information, setting X-ray irradiation conditions (SID, a tube voltage, and a tube current, etc.) and an image scaling rate, photography sequence selection (e.g., rotation photography), setting of a position and a direction for imaging a subject, and various command inputs (e.g., a photography start command, etc.) can be carried out. Setting an ROI fluoroscopy or spot fluoroscopic region, switching from normal photography to photography using the high-definition detector 112, and switching from spot fluoroscopy or ROI fluoroscopy to normal photography can be carried out by operating the input interface circuitry 19.

The processing circuitry 17 has a system control program 171, a drive control program 172, an X-ray control program 173, an image computation process program 174, a detector switching control program 175, a display control program 176, and misalignment control program 177. The processing circuitry 17 realizes the processing functions corresponding to the programs 171 to 177 by executing the programs 171 to 177.

The processing function of the system control program 171 temporarily stores information, such as command signals input by the operator through the input interface circuitry 19 and various initial setting conditions, etc., and then transmits the information to each of the processing functions of the processing circuitry 17.

The processing function of the drive control program 172 controls the C-arm drive apparatus 122 and the top board drive apparatus 13 using information related to the drive of the C-arm 12 and the top board 15 which is input from the input interface circuitry 19.

The processing function of the X-ray control program 173 reads the information from the processing function of the system control program 171 to control the X-ray irradiation conditions, such as a tube current, a tube voltage, and an irradiation duration, etc. at the high-voltage generation apparatus 5.

The processing function of the image computation processing program 174 obtains the projection data from the memory circuitry 16 to generate an X-ray image, and performs image computation processing to display an LIH (Last Image Hold) image 23. The LIH image 23 is an X-ray image obtained by performing photography or fluoroscopy on a region including the ROI region to which spot fluoroscopy is to be performed. The processing function of the image computation processing program 174 is to display the LIH image 23 as a reference image in the non-irradiated region near the ROI of the spot fluoroscopy when the spot fluoroscopy begins. By displaying the LIH image 23, a fluoroscopy image continues to be displayed in a periphery region outside of the spot fluoroscopic region 24 even when the spot fluoroscopy is being carried out, and this makes it easier for the operator to visually recognize the ROI and the periphery region thereof and to understand the position of the ROI with respect to the entire X-ray image. It should be noted that the LIH image 23 is preferably an X-ray image obtained by performing photography or fluoroscopy immediately before performing the spot fluoroscopy.

The processing function of the detector switching control program 175 is to control switching of a photography mode between a normal photography mode which uses the X-ray detector 111, and a high-definition photography mode which uses the high-definition detector 112 in addition to the X-ray detector 111. When the processing function of the detector switching control program 175 reads the information about the photography mode switching which is input by the operator through the input interface circuitry 19, the photography mode is switched from the normal photography mode to the high-definition photography mode or vice-versa. The photography mode may be switched by a foot switch used for fluoroscopy or by an input operation at a main console, etc.

Upon switching the photography mode, a signal indicating that switching of the X-ray detector 111 or the high-definition detector 112 is to be carried out is transmitted to the processing function of the drive control program 172. The processing function of the drive control program 172 drives the C-arm, etc. in accordance with received information. In the X-ray detector apparatus 11 with the one-panel configuration in which the X-ray detector 111 and the high-definition detector 112 are integrated, when the switching to the high-definition mode is carried out, X-rays irradiated onto the X-ray detector apparatus 112 are detected by both the X-ray detector 111 and the high-definition detector 112. In the X-ray detector apparatus 11 with the two-panel configuration in which the X-ray detector 111 and the high-definition detector 112 are separately driven, the arm, etc. holding the high-definition detector 112 is driven upon the switching to the high-definition mode, and the high-definition detector 112 is moved to a position in front of the X-ray detector 111 so as to be able to detect X-rays. Upon the switching of the photography mode, the processing function of the detector switching control program 175 transmits a signal indicating a change of X-ray irradiation conditions to the X-ray control program 173. For example, since the high-definition detector 112 has more X-ray detecting elements than the X-ray detector 111, the X-ray exposure detected at each X-ray detecting element is less. For this reason, in the case of using the high-definition detector 112, it is necessary to set a higher tube voltage than the voltage for normal photography so that an irradiation amount of X-rays is increased.

The processing function of the display control program 176 reads a signal from the processing function of the system control program 171 at the time of performing the spot fluoroscopy or the ROI fluoroscopy to carry out a control to display an X-ray image based on desired X-ray image data obtained from the memory circuitry 16 and a control to transfer to an enlarged display of a fluoroscopic region. This corresponds to the displaying of the enlarged spot fluoroscopic region 24 or the ROI fluoroscopic region 26 in FIGS. 6 and 8, which will be described later. The processing function of the display control program 176 carries out a control of a transfer from an enlarged display of the fluoroscopic region to the normal fluoroscopic display, and control of a transfer from a normal fluoroscopic display to an enlarged display.

The processing function of the misalignment control program 177 moves, by the control of the C-arm drive apparatus 122, both of the X-ray detector 111 and the high-definition detector 112, or only the high-definition detector 112 so that the detection region of the high-definition detector 112 includes an irradiation region of the subject P, which is formed by the opening region based on the position of the opening region. Specifically, for example, both of the X-ray detector 111 and the high-definition detector 112, or only the high-definition detector 112 may be moved so that the center coordinate of the X-ray irradiation region of the subject P which is formed by the opening region matches the center coordinate of the detection region 22 of the high-definition detector 112. In this case, the misalignment among the X-ray diaphragm 103, the center coordinate of the opening region of the ROI filter 102, and the center coordinate of the opening region of the high-definition detector 112 is calculated. At this time, the high-definition detector 112 is moved in such a manner that an area size, where the X-ray irradiation region of the subject P formed by the opening region and the detection region 22 of the high-definition detector 112 match, achieves maximum. For example, the X-ray diaphragm drive apparatus 28 is referred to for the center coordinate information of the opening region of the X-ray diaphragm 103 at the time of performing the spot fluoroscopy, and the ROI filter drive apparatus 29 is referred to for the center coordinate information of the ROI filter 102 at the time of performing the ROI fluoroscopy, and calculating a misalignment between the central coordinates of the respective detection regions. The processing function of the misalignment control program 177 performs a control using the calculated difference between the center coordinates in such a manner that the C-arm 12 is moved by the C-arm drive apparatus 122, and the opening region of the X-ray diaphragm 103 of the X-ray generation apparatus 10 or the center position of the ROI filter 102 matches with the central position of the detection region 22 of the high-definition detector 112.

The processing function of the misalignment control program 177 moves both of the X-ray detector 111 and the high-definition detector 112, or only the high-definition detector 112 so that the move distance of the high-definition detector 112 is shortest with respect to the irradiation region of the subject P formed by the opening region. For example, a misalignment may be detected so as to include the spot fluoroscopic region 24 or the ROI fluoroscopic region 26 in the detection region 22 of the high-definition detector 112, and the detection region of the high-definition detector 112 may be moved for a shortest distance. For a further example, the detection region of the high-definition detector 112 may be moved for a shortest distance so that a difference between the first and second sides of the square indicating the detection region 22 of the high-definition detector 112 and those of the square indicating the spot fluoroscopic region 24 becomes 0.

In both examples, the size of the opening region does not change when the X-ray detector 111 and the detection region 22 are moved, or when the detection region 22 is moved.

The system control program 171, the drive control program 172, the X-ray control program 173, the image computation process program 174, the detector switching control program 175, the display control program 176, and the misalignment control program 177, which are the constituent elements of the processing circuitry 17, are stored in the memory circuitry 16 in the form of a program executable by the computer. The processing circuitry 17 is a processor which realizes the functions respectively corresponding to the programs by reading a program from the memory circuitry and executing the program. In other words, the processing circuitry 17 in a state where each of the programs is read has each of the programs shown in the processing circuitry of FIG. 1. It was described with reference to FIG. 1 that the processing functions which are performed in the system control program 171, the drive control program 172, the X-ray control program 173, the image computation process program 174, the detector switching control program 175, the display control program 176, and the misalignment control program 177 are realized in a single processing circuitry 17; however, a plurality of independent processors may be combined to constitute the processing circuitry 17, and the functions may be realized by a program by each of the processors.

Next, the switching between the fluoroscopic mode and the display mode is described with reference to the flowchart of FIG. 4. The switching procedure that takes place during the spot fluoroscopy will be described with reference to the flowchart; however, the switching between the fluoroscopic mode and the display mode is also the same for the ROI fluoroscopy. A foot switch, for example, is used for switching between the fluoroscopic mode and the display mode.

In step ST1, when the foot switch for the normal fluoroscopy mode for performing fluoroscopy on the entire fluoroscopic region is pressed by the operator, X-ray fluoroscopy for the entire fluoroscopic region is performed.

In step ST2, an ROI is set by the operator. The operator refers to an X-ray image displayed on the display circuitry 18 to set an ROI through the input interface circuitry 19. If no ROI is set, X-ray fluoroscopy for the entire fluoroscopic region continues without an ROI.

In step ST3, a foot switch for the spot fluoroscopy is pressed by the operator instead of the foot switch for the normal fluoroscopy mode, the spot fluoroscopy is performed for the ROI which was set in step ST2 (step ST4). If the foot switch is not pressed by the operator, the X-ray fluoroscopy for the entire fluoroscopic region continues.

When the spot fluoroscopy is performed in step ST4, the operator carries out the high-definition photography mode through the input interface circuitry 19, pressing the foot switch for the spot fluoroscopy (step ST5). If the high-definition photography mode is not carried out, the spot fluoroscopy continues. If the high-definition photography mode is carried out in step ST5, a misalignment between the spot fluoroscopic region 24 and the detection region 22 of the high-definition detector 112 is automatically detected in step ST6.

If a misalignment is detected in step ST6, a necessity of position correction is automatically determined in step ST7. For example, even when the center coordinate of the spot fluoroscopic region 24 and that of the detection region 22 of the high-definition detector 112 do not match, as long as the entire spot fluoroscopic region 24 is included in the detection region 22, the high-definition detector may not have to be moved. If position correction is not necessary, the process proceeds to step ST9, and the high-definition fluoroscopy is automatically carried out.

If position correction is determined to be necessary in step ST7, position correction is performed in step ST8 in such a manner that the detection region 22 of the high-definition detector 112 is moved automatically so as to include the entire spot fluoroscopic region 24.

If position correction is performed in step ST8, the high-definition fluoroscopy is automatically performed in step ST9. In step ST9, the operator may operate the input interface circuitry 19 for enlarging the display of the high-definition fluoroscopic region to perform switching the display to an enlarged display.

In step ST10, when the operator ends the high-definition photography mode through the input interface circuitry 19, the high-definition mode is ended. If the operation to end the high-definition photography mode is not performed by the operator, the high-definition fluoroscopy continues.

In step ST10, under the state where the high-definition mode is no longer continued, the spot fluoroscopy is ended when the operator stops pressing the spot fluoroscopy foot switch, and the fluoroscopy process is ended. If the operator continues to press the spot fluoroscopy foot switch, the process returns to step ST4 and the spot fluoroscopy continues.

In the flowchart, carrying out the switching to the high-definition photography mode through the input interface circuitry 19 was explained; however, the switching may be operated through a foot switch, similarly to the other steps of the process. In this case, the switching to the high-definition photography mode is realized when the operator presses a foot switch used for the high-definition photography mode. The end of the high-definition photography mode is realized by stopping pressing the foot switch. At the same time when the high-definition photography is ended, the X-ray irradiation is also ended.

According to the series of operations as described above, the operator switches the fluoroscopy to the high-definition photography mode after the spot fluoroscopy or the ROI fluoroscopy to automatically obtain a high-definition image of the ROI at the time of the fluoroscopy.

FIG. 5 shows an example of a method of moving the X-ray detection apparatus 11 in order to perform a position correction of the spot fluoroscopic region 24 and the detection region 22 of the high-definition detector 112 when the spot fluoroscopy is performed. FIG. 5 is a schematic diagram showing a relative position relationship among the detection region 21 of the X-ray detector 111, the detection region 22 of the high-definition detector 112, and a blood vessel 31. The arrangement of the detection region 21 of the X-ray detector 111 and the detection region 22 of the high-definition detector 112 as shown in FIG. 5 (a) is defined as an initial arrangement. A situation where a stent 32 (not shown) is embedded at the distal end of the blood vessel 31 is taken as an example. In order to observe the stent 32 at the distal end of the blood vessel 31, after setting the spot fluoroscopic region 24 as shown in FIG. 5 (b), the center position of the detection region 22 of the high-definition detector 112 is moved so as to match with the center position of the spot fluoroscopic region 24 as shown in FIG. 5 (c). If the configuration shown in FIG. 2A or 2B in which the high-definition detector 112 and the X-ray detector 11 are integrated is used as the X-ray detection apparatus 11, the detection region 21 of the X-ray detector 111 is also moved along with the detection region 22 of the high-definition detector 112.

FIG. 6 shows an example of the display of the enlarged high-definition image 25 after the X-ray detection apparatus 11 is moved as shown in FIG. 5 (c), and the switching to the high-definition photography mode is carried out after the spot fluoroscopy. Since a high-definition image can be obtained by the high-definition detector 112 for the spot fluoroscopic region 24 and the detection region 22 of the high-definition detector 112 including the spot fluoroscopic region 24 is enlarged and displayed, it becomes possible to observe the stent 32 disposed at the distal end of the blood vessel 31. The detection region 22 of the high-definition detector 112 may select X-ray detection elements to output in accordance with the shape of the spot fluoroscopic region 24. In other words, only the spot fluoroscopic region 24 may be configured as a detection region 22b of the high-definition detector 112, and the region other than the spot fluoroscopic region 24 may be displayed using the LIH image 23, or the spot fluoroscopic region 24 may be enlarged and displayed in a desired shape. For example, if the spot fluoroscopic region 24 is smaller than the detection region 22 of the high-definition detector 112, the high-definition detector 112 does not use all the detection elements in the detection region 22 of the high-definition detector 112 to detect X-rays; rather, the detector 112 detects only the X-rays that pass the spot fluoroscopic region 24, and X-rays outside of the spot fluoroscopic region 24 may be detected by the X-ray detector 111. Using the high-definition detector 112 only for the spot fluoroscopic region 24 results in narrowing the region for which the X-ray detection elements of the high-definition detector 112 are used, and an amount of projection data is reduced, thereby improving the image processing speed when image data is generated.

Figure 7:
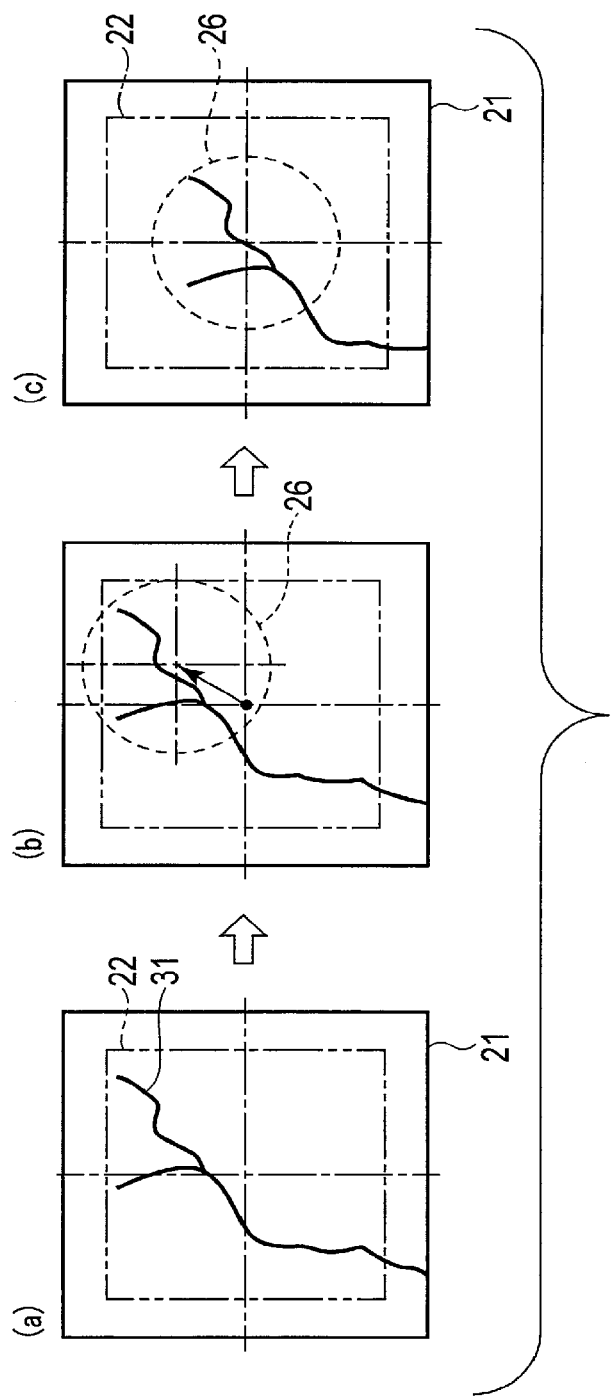
FIG. 7 is a diagram showing an example of the automatic positioning mechanism at the time of carrying out ROI fluoroscopy at the X-ray image diagnosis apparatus according to the embodiment.

FIG. 7 shows an example of a method of moving the X-ray detection apparatus 11 in order to perform a position correction of the ROI fluoroscopic region 26 and the detection region 22 of the high-definition detector 112 when the ROI fluoroscopy is performed. FIG. 7 is a schematic diagram showing a relative position relationship among the detection region 21 of the X-ray detector 111, the detection region 22 of the high-definition detector 112, and a blood vessel 31. The arrangement of the detection region 21 of the X-ray detector 111 and the detection region 22 of the high-definition detector 112 as shown in FIG. 7 (a) is defined as an initial arrangement. Similar to the example of FIG. 5, suppose the stent 32 (not shown) embedded in the distal end portion of the blood vessel 31 is observed. If the distal end portion of the blood vessel 31 is set as the ROI fluoroscopic region 26 by the operator as shown in FIG. 7 (b), the center position of the detection region 22 of the high-definition detector 112 is moved so as to match with the center position of the ROI fluoroscopic region 26 as shown in FIG. 7 (c). If the configuration shown in FIG. 2A or 2B in which the high-definition detector 112 and the X-ray detector 11 are integrated is used as the X-ray detection apparatus 11, the detection region 21 of the X-ray detector 111 is also moved along with the detection region 22 of the high-definition detector 112.

Figure 8:
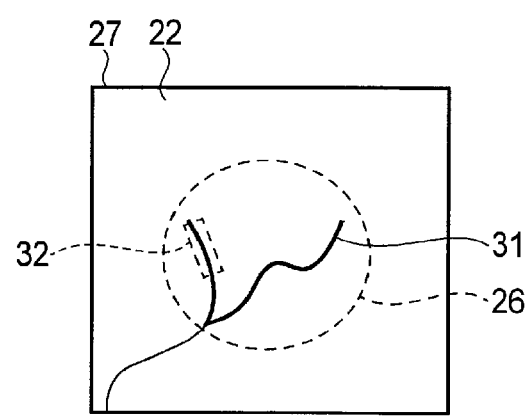
FIG. 8 is a diagram showing an example of a display region after carrying out ROI fluoroscopy according to the embodiment.

FIG. 8 shows an example of the display of the enlarged high-definition image 27 after switching to the high-definition photography mode is carried out after the ROI fluoroscopy. It becomes possible to observe the stent 32 in the blood vessel 31 when a high-definition image is acquired by the high-definition detector 112 for the ROI fluoroscopic region 26. Only the ROI fluoroscopic region may be enlarged and displayed, instead of displaying an image of the ROI fluoroscopic region 26 and an image of the region other than the ROI fluoroscopic region 26 with a low S/N ratio, like those shown in FIG. 8. The detection region 22 of the high-definition detector 112 may be configured in a desired shape in accordance with the shape of the ROI filter 102 at the time of ROI fluoroscopy. In other words, only the ROI fluoroscopic region 26 may be configured as the detection region 22c of the high-definition detector 112, and the region other than the ROI fluoroscopic region 26 may be displayed in the detection region 21 of the X-ray detector 111. The ROI fluoroscopic region 26 in the desired shape may be enlarged and displayed. For example, if the ROI fluoroscopic region 26 is smaller than the detection region 22 of the high-definition detector 112, the high-definition detector 112 may detect only the X-rays that pass the ROI fluoroscopic region 26, and does not have to use all the detection elements of the detection region 22 to detect X-rays. At this time, the X-rays outside of the ROI fluoroscopic region 26 may be detected by the X-ray detector 111. Using the high-definition detector 112 only for the ROI fluoroscopic region 26, similarly to the case of spot fluoroscopy, results in narrowing the region for which the X-ray detection elements of the high-definition detector 112 are used, and an amount of projection data is reduced, thereby improving the image processing speed when image data is generated. In the case of the high-definition detector 112 which has a configuration shown in FIG. 2A or 2B, X-rays are detected by both of the X-ray detector 111 and the high-definition detector 112. Accordingly, X-rays outside of the ROI fluoroscopic region 26 are detected using the X-ray detector 11. Since an area for detecting X-rays in the X-ray detector 111 is larger than that of the high-definition detector 112, X-rays can be easily input, and an image with a greater S/N ratio can be obtained compared to the case of using the high-definition detector 112. Thus, narrowing the region for which the high-definition detector 112 is used can make it possible to reduce noise in an X-ray image to be output.

In the present embodiment, an example is given where the detection region 22 of the high-definition detector 112 is aligned to the X-ray diaphragm 103 or the ROI filter 102; however, the alignment may be achieved by displaying a boundary, etc. of the spot fluoroscopic region 24 or the ROI fluoroscopic region 26 to be displayed on the display circuitry 18, and using coordinate information on the image, instead of using the position of the X-ray diaphragm 103 or the ROI filter 102. For example, the boundary, etc. indicating the boundary of the ROI under fluoroscopy is displayed on the display circuitry 18, and the position information, etc. of the ROI under fluoroscopy on the displayed screen is read and detected as the ROI under fluoroscopy, and the position information is output to the processing function of the misalignment control program 177, and the detection region 22 of the high-definition detector 112 is moved.

In the present embodiment, the X-ray image diagnosis apparatus having an C-arm-shaped holding apparatus was given as an example; however, the embodiment is not limited to the form described in the present embodiment as long as the X-ray image diagnosis apparatus has a mechanism capable of controlling a relative position relationship between the subject P and the X-ray detection apparatus 11. For example, the present embodiment is applicable to an X-ray image diagnosis apparatus having a structure in which the X-ray generation apparatus 10 is hung from the ceiling and the X-ray detection apparatus 11 is set under a bed, or an X-ray TV apparatus, etc. in which mainly a bed moves in different directions.

Contrary to the present embodiment, an ROI under fluoroscopy may be set at a position of the detection region 22 of the high-definition detector 112, and switching to spot fluoroscopy or to ROI fluoroscopy may be performed. For example, a configuration may be provided in which the processing function of the control program 177 reads the detection region 22 of the high-definition detector 112 upon performing spot fluoroscopy or ROI fluoroscopy, and the ROI on which the fluoroscopy is carried out is set so as to match, for example, the center position of the detection region 22 of the high-definition detector 112.

At the time of switching from the high-definition photography mode to the normal photography mode, the spot fluoroscopy image or the ROI fluoroscopy image having the fluoroscopy position at its center before position alignment of the detection region 22 of the high-definition detector 122 and the ROI under fluoroscopy may be displayed once again. Or, a spot fluoroscopic image with the ROI under fluoroscopy in the high-definition photography mode with the LIH image 23 being displayed on the periphery or an ROI fluoroscopic image may be displayed. If the spot fluoroscopic image and LIH image 23 are displayed, photography for an LIH image 23 having the ROI under fluoroscopy as its center is performed once again.

Variation Example 1

Figure 9:
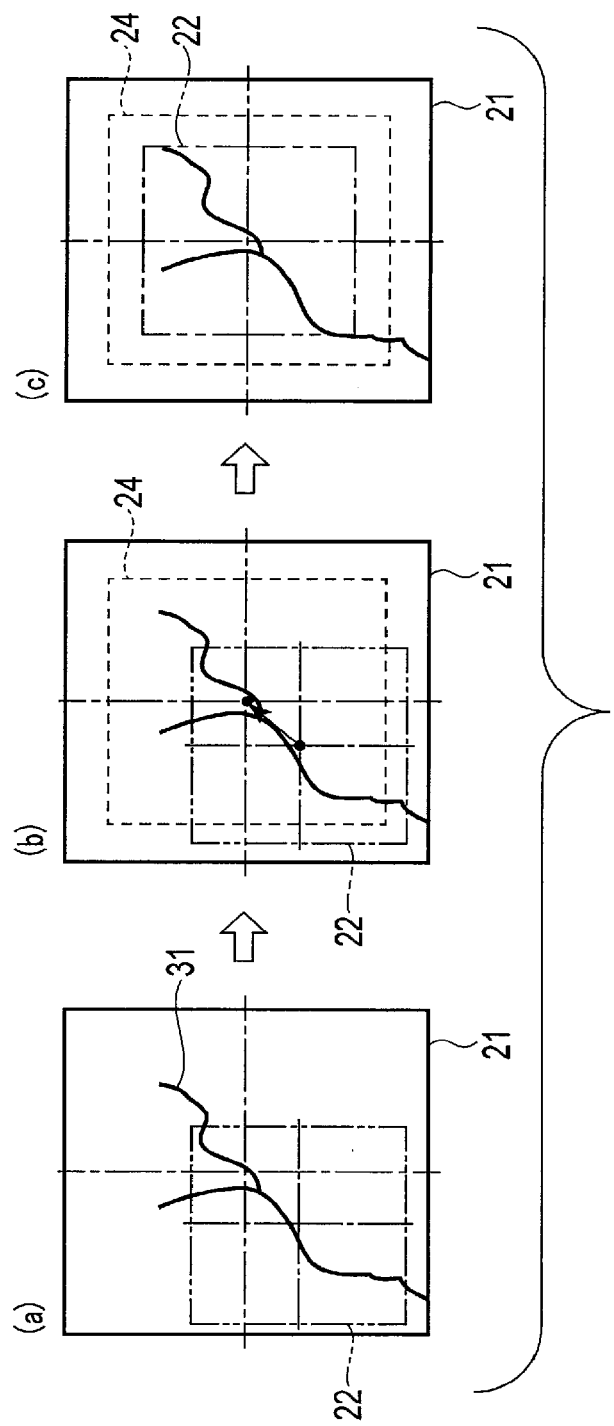
FIG. 9 is a diagram showing an example of a method of moving the high-definition detector according to the embodiment.

Next, a case where the spot fluoroscopic region 24 is larger than the detection region 22 of the high-definition detector 112, which is a variation example of the present embodiment, will be explained with reference to FIG. 9. The arrangement of the detection region 21 of the X-ray detector 111 and the detection region 22 of the high-definition detector 112 as shown in FIG. 9 (*a*) is defined as an initial arrangement. A Suppose if a spot fluoroscopic region 24 larger than the detection region 22 of the high-definition detector 112 is set as shown in FIG. 9 (*b*). In this case, a configuration in which the detection region 22 of the high-definition detector 112 is moved in such a manner so that an area overlapping the spot fluoroscopic region 24 becomes the largest as shown in FIG. 9 (*c*), and the center of the detection region 22 matches the spot fluoroscopic region 24.

Variation Example 2

Figure 10:
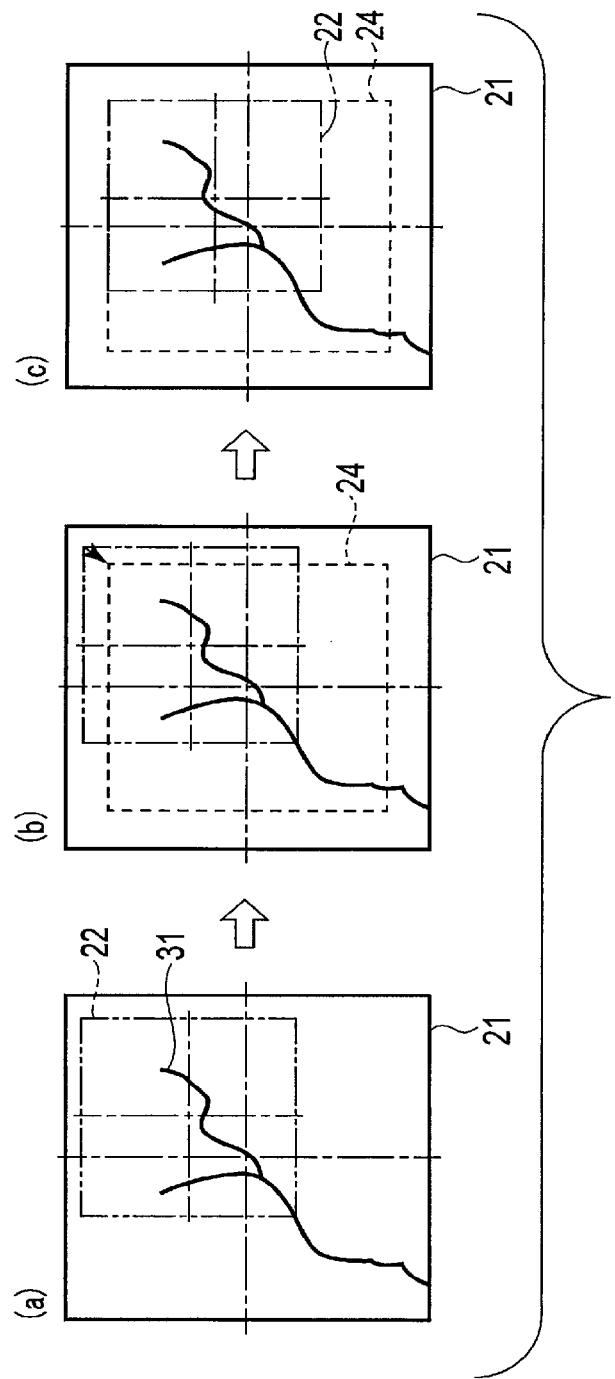
FIG. 10 is a diagram showing an example of a method of moving the high-definition detector according to the embodiment.

A case where the detection region 22 of the high-definition detector 112 is moved in such a manner that the detection region 22 overlaps the spot fluoroscopic region 24 and the moving distance becomes shortest will be explained, as shown in FIG. 10 as another example. The arrangement of the detection region 21 of the X-ray detector 111 and the detection region 22 of the high-definition detector 112 as shown in FIG. 10 (*a*) is defined as an initial arrangement. If the spot fluoroscopic region 24 is set in proximity to the detection region 22 of the high-definition detector 112 as shown in FIG. 10 (*b*), the detection region 22 of the high-definition detector 112 may be moved in such a manner that the entire detection region 22 overlaps the spot fluoroscopic region 24, and the moving distance of the high-definition detector 112 is minimized without having the center positions not overlap as shown in FIG. 10 (*c*). The case where the spot fluoroscopic region 24 is larger than the detection region 22 of the high-definition detector 112 is explained with FIG. 10; however, the present variation example is applicable to the case where the detection region 22 of the high-definition detector 112 is larger than the spot fluoroscopic region 24.

Either the variation example 1 or the variation example 2 may be selected by the method of moving the high-definition detector 112 in the case where the spot fluoroscopic region 24 is larger than the detection region 22 of the high-definition detector 112, they may be set to be selected by the operator. A similar operation using the above method of moving may be performed on the ROI fluoroscopic region 26 at the time of performing the RIO fluoroscopy.

According to the above-explained embodiment, a high-definition image of the spot fluoroscopic region or the ROI fluoroscopic region can be obtained by automatically moving the detection region 22 of the high-definition detector 112 to the ROI under fluoroscopy, using the position of the ROI filter 102 or the X-ray diaphragm 103. It is possible to match the detection region 22 of the high-definition detector 112 automatically to the ROI under fluoroscopy. Thus, there is no necessity of manually moving the C-arm 12 or a bed, etc., or displaying a marker, etc. used for position alignment on a display screen to perform an alignment of the ROI and the detection region 22 of the high-definition detector 112 based on the marker. Accordingly, it is easy and convenient for the operator to operate, and it is possible to shorten an examination time and to reduce the exposure. Furthermore, the automatic position alignment shortens the examination time or a treatment time, thereby mitigating stress on the subject (patient).

The high voltage generation apparatus 5, the X-ray generation apparatus 10, the X-ray tube 101, the ROI filter 102, the X-ray diaphragm 103, the X-ray detection apparatus 11, the X-ray detector 111, the C-arm 12, the C-arm state detector 121, the C-arm drive apparatus 122, the top board drive apparatus 13, the memory circuitry 16, the processing circuitry 17, the system control program 171, the drive control program 172, the X-ray control program 173, the image computation processing program 174, the detector switching control program 175, the display control program 176, the misalignment control program 177, the display circuitry 18, the input interface circuitry 19, the X-ray diaphragm drive apparatus 28, and the ROI filter drive apparatus 29 in each of the embodiments may be realized by the high voltage generation unit 5, the X-ray generation unit 10, the X-ray tube unit 101, the ROI filter unit 102, the X-ray diaphragm unit 103, the X-ray detection unit 11, the X-ray detection unit 111, the C-arm unit 12, the C-arm state detection unit 121, the C-arm drive unit 122, the top board drive unit 13, the memory circuitry unit 16, the processing unit 17, the system control unit 171, the drive control unit 172, the X-ray control unit 173, the image computation processing unit 174, the detector switch control unit 175, the display control unit 176, the misalignment control unit 177, the display unit 18, the input interface unit 19, the X-ray diaphragm drive unit 28, and the ROI filter drive unit 29, respectively. The operation of the constituent elements explained as "units" in the present embodiment may be realized by hardware, software, or a combination thereof.

It should be noted that the expression "processor" used in the above explanation means circuitry, such as a CPU (central processing unit), GPU (Graphics Processing Unit), Application Specific Integrated Circuit (ASIC), or a programmable logic device (for example, a Simple Programmable Logic Device (SPLD), Complex Programmable Logic Device (CPLD), and Field Programmable Gate Array (FPGA)), etc. The processor realizes its function by reading and executing the program stored in the memory circuitry. Instead of storing a program on the memory circuitry, the program may be directly integrated into the circuitry of the processor. In this case, the function is realized by reading and executing the program integrated into the circuitry. Each processor of the present embodiment is not limited to a case where each processor is configured as a single circuit; a plurality of independent circuits may be combined into one processor to realize the function of the processor. Furthermore, a plurality of constituent elements shown in FIG. 1 may be integrated into one processor to realize the function.

The X-ray tube 101 in the embodiment is an example of the X-ray generator in the claims. The ROI filter 102 and the X-ray diaphragm 103 in the embodiment are an example of the X-ray restriction unit in the claims. The first X-ray detector 111 in the embodiment is an example of the first X-ray detector in the claims. The high-definition detector 112 in the embodiment is an example of the second X-ray detector in the claims. The C-arm 12, the C-arm state detector 121, the C-arm drive apparatus 122, the processing circuitry 17, and the drive control program 172 in the embodiment are an example of the drive in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray image diagnosis apparatus, comprising:
   an X-ray generator configured to generate X-rays to irradiate a subject;
   an X-ray restriction unit which is disposed between the subject and the X-ray generator to form an opening region using a metal plate, and which restricts X-rays outside the opening region among the X-rays;
   a first X-ray detector which has a first detection region in which X-rays that pass through the subject are detected;
   a second X-ray detector which has a second detection region which is smaller than the first detection region and which has a high spatial resolution; and
   a drive configured to move, based on a position of the opening region, the first X-ray detector and the second X-ray detector so that the second detection region includes an irradiation region of the subject formed by the opening region.

2. The X-ray image diagnosis apparatus according to claim 1, wherein the second X-ray detector is attached in such a manner that the second detection region overlaps the first detection region.

3. The X-ray image diagnosis apparatus according to claim 1, wherein the second X-ray detector is disposed inside the first X-ray detector, and attached integrally with the first X-ray-detector.

4. The X-ray image diagnosis apparatus according to claim 1, wherein the X-ray restriction unit is an X-ray diaphragm which shields X-rays outside of the opening region.

5. The X-ray image diagnosis apparatus according to claim 1, wherein the X-ray restriction unit is a filter which attenuates X-rays outside of the opening region.

6. The X-ray image diagnosis apparatus according to claim 1, wherein the drive moves the first X-ray detector and the second X-ray detector in such a manner that a center coordinate of the X-ray irradiation region of the subject which is formed by the opening region matches a center coordinate of the second detection region.

7. The X-ray image diagnosis apparatus according to claim 1, wherein the drive moves the first X-ray detector and the second X-ray detector in such a manner that the moving distance of the second X-ray detector is reduced with respect to the irradiation region of the subject formed by the opening region.

8. The X-ray image diagnosis apparatus according to claim 1, wherein the movements of the first X-ray detector and the second X-ray detector are executed based on input information from an operator.

9. The X-ray image diagnosis apparatus according to claim 1, wherein a size of the opening region does not change when the first X-ray detector and the second detection region are moved.

10. An X-ray image diagnosis apparatus, comprising:
    an X-ray generator configured to generate X-rays to irradiate a subject;
    an X-ray restriction unit which is disposed between the subject and the X-ray generator to form an opening region using a metal plate, and which restricts X-rays outside the opening region among the X-rays;
    a first X-ray detector which has a first detection region in which X-rays that pass through the subject are detected;
    a second X-ray detector which has a second detection region which is smaller than the first detection region and which has a high spatial resolution; and
    a drive configured to move, based on a position of the opening region, the second X-ray detector so that the second detection region includes an irradiation region of the subject formed by the opening region.

11. The X-ray image diagnosis apparatus according to claim 10, wherein the second X-ray detector is disposed separately from the first X-ray detector and is independently movable from the first X-ray detector.

12. The X-ray image diagnosis apparatus according to claim 10, wherein the X-ray restriction unit is an X-ray diaphragm which shields X-rays outside of the opening region.

13. The X-ray image diagnosis apparatus according to claim 10, wherein the X-ray restriction unit is a filter which attenuates X-rays outside of the opening region.

14. The X-ray image diagnosis apparatus according to claim 10, wherein the drive moves the second X-ray detector in such a manner that a center coordinate of the X-ray irradiation region of the subject which is formed by the opening region matches a center coordinate of the second detection region.

15. The X-ray image diagnosis apparatus according to claim 10, wherein the drive moves the second X-ray detector in such a manner that the moving distance of the second X-ray detector is reduced with respect to the irradiation region of the subject formed by the opening region.

16. The X-ray image diagnosis apparatus according to claim 10, wherein the movement of the second X-ray detector is executed based on input information from an operator.

17. The X-ray image diagnosis apparatus according to claim 10, wherein a size of the opening region does not change when the second detection region is moved.

* * * * *